United States Patent
Reddy et al.

(10) Patent No.: US 7,434,581 B1
(45) Date of Patent: Oct. 14, 2008

(54) CONDOMS FOR REDUCING FAILURE RATE AND EXTENDING PLEASURE

(76) Inventors: Alla V. K. Reddy, 9 Webster Ct., Plainsboro, NJ (US) 08536; Ravikumar Reddy Alla, 5876 155th Ave. SE., Bellevue, WA (US) 98006; Madhusudhan Reddy Alla, 938 Sunset Ridge, Bridgewater, NJ (US) 08807; Raghunatha Reddy Alla, 54 Mercer St., Apt. 1, Jersey City, NJ (US) 07302

( * ) Notice: Subject to any disclaimer, the term of this patent is extended or adjusted under 35 U.S.C. 154(b) by 0 days.

(21) Appl. No.: 11/778,010

(22) Filed: Jul. 13, 2007

Related U.S. Application Data (60) Provisional application No. 60/928,045, filed on May 7, 2007, provisional application No. 60/926,250, filed on Apr. 25, 2007.

(51) Int. Cl.
*A61F 6/02* (2006.01)
*A61F 6/04* (2006.01)
*A61F 5/44* (2006.01)

(52) U.S. Cl. .................. 128/844; 128/842; 128/918; 604/347

(58) Field of Classification Search ............ 604/347, 604/349, 352, 364; 128/842, 844, 918; 424/34.1, 424/443, 44.3; 428/35.5, 36.8, 36.9; 600/38–40
See application file for complete search history.

(56) References Cited

U.S. PATENT DOCUMENTS

| | | | |
|---|---|---|---|
| 2,410,460 A | 11/1946 | Robinson | |
| 2,586,674 A | 2/1952 | Lonne | |
| 4,009,717 A | 3/1977 | Allen | |
| 4,432,357 A | 2/1984 | Pomeranz | |
| 4,795,425 A | 1/1989 | Pugh | |
| 4,855,169 A | 8/1989 | McGlothlin et al. | |
| 4,910,803 A | 3/1990 | Cukier | |
| 4,934,382 A | 6/1990 | Barone, Jr. | |
| 5,024,852 A | 6/1991 | Busnel et al. | |
| 5,045,341 A | 9/1991 | Shlenker | |
| 5,050,619 A | 9/1991 | Ferguson | |
| 5,082,004 A | 1/1992 | Reddy | |

(Continued)

FOREIGN PATENT DOCUMENTS

EP 0645128 9/1994

(Continued)

*Primary Examiner*—Patricia Bianco
*Assistant Examiner*—Brandon Jackson
(74) *Attorney, Agent, or Firm*—Mattingly, Stanger, Malur & Brundidge, P.C.

(57) ABSTRACT

A condom with reduced chance of failure includes an inner pouch within an outer pouch. The inner pouch is bonded to the outer pouch adjacent to their open ends to form a sealed interstitial space between the inner and outer pouches. A lubricant is located in the interstitial space to enable the outer pouch to slide relative to the inner pouch during sexual intercourse. The outer pouch has an enlarged head area so that the outer pouch easily slides back and forth over the inner pouch and glans of the penis during intercourse. The inner pouch has a wall thickness that is less than the wall thickness of the outer pouch for increased sensitivity. The inner pouch has a narrow segment extending into a smaller bulb exerting pressure at the junction of the glans and shaft covering the entire frenulum area, thereby inhibiting premature ejaculation and reducing slippage.

19 Claims, 6 Drawing Sheets

U.S. PATENT DOCUMENTS

| | | | |
|---|---|---|---|
| 5,102,405 A | 4/1992 | Conway et al. | |
| 5,191,902 A | 3/1993 | Wilk | |
| 5,284,159 A | 2/1994 | Wilk | |
| 5,331,974 A | 7/1994 | Sook | |
| 5,351,698 A | 10/1994 | Wheeler et al. | |
| 5,425,379 A | 6/1995 | Broad, Jr. | |
| 5,454,379 A | 10/1995 | Shepherd | |
| 5,486,322 A | 1/1996 | Fuchs | |
| 5,513,652 A | 5/1996 | Schwartz | |
| 5,513,654 A | 5/1996 | Delson | |
| 5,549,924 A | 8/1996 | Shlenker et al. | |
| 5,577,514 A | 11/1996 | Zimmerman | |
| 5,579,784 A | 12/1996 | Harari | |
| 5,606,982 A | 3/1997 | Piotti | |
| 5,622,186 A | 4/1997 | Schwartz | |
| 5,623,945 A | 4/1997 | Shecterle et al. | |
| 5,626,149 A | 5/1997 | Schwartz | |
| 5,679,399 A | 10/1997 | Shlenker et al. | |
| 5,694,948 A | 12/1997 | Jahangiri-Famenini | |
| 5,836,307 A * | 11/1998 | Scholl | 128/844 |
| 5,927,278 A | 7/1999 | Omrani | |
| 5,965,276 A * | 10/1999 | Shlenker et al. | 428/492 |
| 6,000,398 A | 12/1999 | Alla et al. | |
| 6,365,278 B1 | 4/2002 | Hoerner et al. | |
| 6,367,477 B2 | 4/2002 | Lee | |
| 6,776,755 B1 * | 8/2004 | Raskin | 600/39 |
| 6,796,311 B1 | 9/2004 | Zurakowski | |
| 6,983,751 B2 | 1/2006 | Osterberg | |
| 2004/0103901 A1 | 6/2004 | Rensburg | |
| 2006/0048784 A1 | 3/2006 | Turner | |
| 2006/0169287 A1 | 8/2006 | Harrison et al. | |
| 2006/0264856 A1 | 11/2006 | Wong | |
| 2007/0144529 A1 | 6/2007 | Bryant | |

FOREIGN PATENT DOCUMENTS

| | | |
|---|---|---|
| EP | 0745362 | 5/1996 |
| FR | 2616062 | 12/1988 |
| FR | 2642961 | 8/1990 |
| GB | 1300676 | 4/1971 |
| IL | 108250 | 4/1997 |
| JP | 8033664 | 2/1996 |

* cited by examiner

FIG. 3 OUTER POUCH

FIG. 2 INNER POUCH

CONDOMS FOR REDUCING FAILURE RATE AND EXTENDING PLEASURE

CROSS REFERENCES TO RELATED APPLICATIONS

This application claims the benefit of U.S. Provisional Application No. 60/926,250, filed Apr. 25, 2007, and U.S. Provisional Application No. 60/928,045, filed May 7, 2007, both to the same inventors as herein, the entire disclosures of which are incorporated herein by reference.

BACKGROUND OF THE INVENTION

1. Field of the Invention

The present invention relates generally to condoms for use during sexual intercourse.

2. Description of Related Art

With the proliferation of sexually transmitted diseases (STDs), including human immunodeficiency virus (HIV), the virus that causes acquired immune-deficiency syndrome (AIDS), and with the uncontrolled growth of the world's population, there is a pressing unmet need for an effective means for preventing the transmission of STDs and for controlling population growth. One method for accomplishing both these goals is by introducing an effective barrier between male and female sex organs during sexual intercourse for preventing the transmission of bodily fluids and for limiting the actual skin-to-skin contact between the sexual organs. Heretofore, conventional means for creating such barriers have included the use of condoms, diaphragms, prophylactic gels, creams, and the like.

Since ancient times, one successful means for creating a barrier to bodily fluids during sex has been the use of male condoms. Condoms for placement over the penis were originally constructed from animal tissue, and condoms of this type are still in use today. Condoms of animal tissue are generally effective for preventing the passage of semen, but do not prevent the passage of certain microbes, and in particular viruses, such as HIV. Accordingly, most male condoms are now constructed from latex, polyurethane, or other resilient modern polymers that are able to act as a barrier to microbes as well as bodily fluids. While condoms have become popular for the control of STDs and pregnancy worldwide, there is still much room for improvement. For example, many men do not like to use male condoms because such condoms can deaden sensation, thereby causing erectile dysfunction and reduced pleasure.

Additionally, conventional condoms have unacceptable failure rates due to a number of factors, such as breaking of the condom, pin holes in the condom wall, slippage of the condom following ejaculation and other failures caused by poor design or improper usage. A recent study showed that the failure rate of male condoms due to breakage was 15 percent. (See, R A Crosby et al., "Men with Broken Condoms: Who and Why?", Sexually Transmitted Infections, 83(1), pp 71-75, February 2007.) Even though the failure rates are high, people continue to use condoms that break frequently because they lack any better alternative for prevention of STDs and pregnancy. For example, female condoms, contraceptive gels, contraceptive creams, diaphragms and cervical caps all are less effective at preventing pregnancy and the transmission of STDs than male condoms. Further, since the onset of the deadly AIDS epidemic, it has become more important than ever to have a condom with reduced failure rates, and preferably a zero failure rate. Accordingly, there is an ongoing need for a condom having a design that will induce a much lower failure rate.

Additionally, it is believed that every man has his own length of time necessary for reaching ejaculation during sexual intercourse. During intercourse nerve impulses pass from the glans of the penis to the brain via the spinal cord to signal ejaculation. The time to reach ejaculation may vary from less than one minute to any number of minutes, depending on the particular individual's signal mechanisms. Vasodilator drugs, such as Viagra®, while useful for helping a man achieve and maintain an erection, do not have any effect on prolonging the length of time for sexual intercourse. Application of local anesthetics, such as Lidocaine, sensation-reducing creams, and the like, may prolong the time of intercourse, but at same time can severely reduce the pleasure experienced by the male during the intercourse because they essentially numb the nerve endings. Accordingly, it would also be desirable if a condom were able to extend the time which it takes a man to reach ejaculation during intercourse, while still providing pleasurable sensations to both partners.

Related art in the area of the invention includes U.S. Pat. Nos. 5,191,902; 5,425,379; 5,623,945; 5,050,619; 5,045,341; 4,930,522; 5,284,159; 5,102,405; 6,000,398; 5,082,004; 5,331,974; 5,622,186; 5,513,652; 4,009,717; and European Patent Application No. EP0645128, the entire disclosures of which are incorporated herein by reference.

SUMMARY OF THE INVENTION

This invention relates to male barrier contraceptives having a reduced chance of breakage, slippage and pinholes. Embodiments of the contraceptives of the invention are also able to increase the pleasure for both partners, in addition to being able to prolong the length of time for sexual intercourse. The invention provides male prophylactic devices that are worn over the penis to prevent transmission of STDs, including AIDS, and to also prevent pregnancy. The present prophylactic devices are designed to have a reduced failure rate, greater chance of proper usage, and an increased acceptability for use by males. These and other features and advantages of the present invention will become apparent to those of ordinary skill in the art in view of the following detailed description of the preferred embodiments.

BRIEF DESCRIPTION OF THE DRAWINGS

The accompanying drawings, in conjunction with the general description given above, and the detailed description of the preferred embodiments given below, serve to illustrate and explain the principles of the preferred embodiments of the best mode of the invention presently contemplated.

DETAILED DESCRIPTION OF THE INVENTION

In the following detailed description of the invention, reference is made to the accompanying drawings which form a part of the disclosure, and, in which are shown by way of illustration, and not of limitation, specific embodiments by which the invention may be practiced. In the drawings, like numerals describe substantially similar components throughout the several views. Further, the drawings, the foregoing discussion, and following description are exemplary and explanatory only, and are not intended to limit the scope of the invention or this application in any manner.

In some embodiments of the present invention, there are provided prophylactic devices which are adopted to be worn by a person to prevent transmission of STDs and semen, even during strenuous sexual intercourse which might cause breakage in conventional condoms. Some embodiments of the invention include a condom within a condom, having an inner pouch located within an outer pouch to create a double-walled condom with unique attributes. The inner pouch of the double-walled condom includes a narrow segment that exerts a circumferential constrictive pressure immediately below and around the glans penis, which helps extend the amount of time during intercourse before the male reaches ejaculation, and which also prevents the inner condom from sliding relative to the shaft of the penis during intercourse. Further, the outer pouch is sized to be large enough so that the outer film of the outer pouch slides back and forth over the inner pouch to create extra pleasurable sensations during intercourse. The combination of the pressure generated by the inner pouch on the penis and the sliding of the outer pouch on the inner pouch causes a delay in ejaculation combined with increased pleasure. Further, the outer film of the outer pouch sliding over the inner film of the inner pouch, with a lubricant located between the two films, transmits pleasurable sensations to the glans of the penis. The extended pleasure created by the outer film of the condom neutralizes the squeezing pressure effect created by the narrow segment portion of the inner pouch. The pleasurable sensation caused by the outer film enhances neurotransmission of ejaculation signals from the glans penis to the brain, while the narrow portion of the inner pouch helps inhibit premature ejaculation. In other words, the dimensions of the condom of the invention can be designed to enhance pleasure and/or extend the time of intercourse, while particular dimensions of the condom may be varied to increase or reduce one of these attributes with respect to the other attribute. Embodiments of the invention also include a guide that ensures that a condom is not put on inside out. Embodiments of the invention also include a condom with multiple undulations or deviations in the condom body, so that the condom body twists relative to a centerline extending from the opening, such as right and out, and then left and in. Embodiments of the invention also incorporate an enlarged bellows mechanism along a distal end portion of the tubular body of the condom for enabling easy forward and backward movement to provide additional pleasure to both partners.

Figure 2:
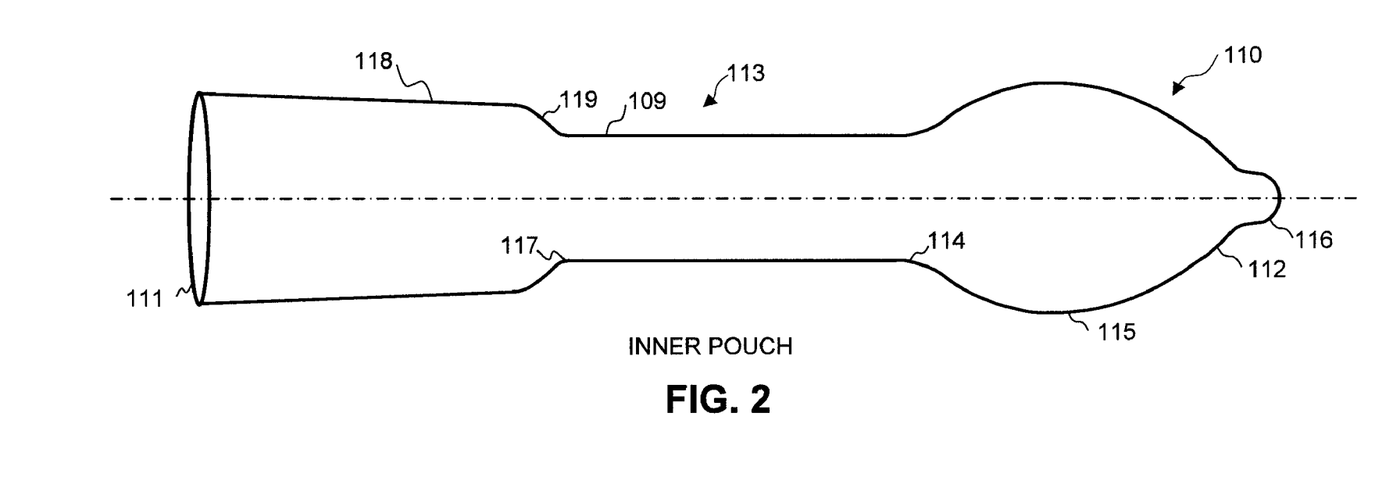
FIG. 2 illustrates an elevation view of the inner pouch of the condom of FIG. 1A.
Figure 3:
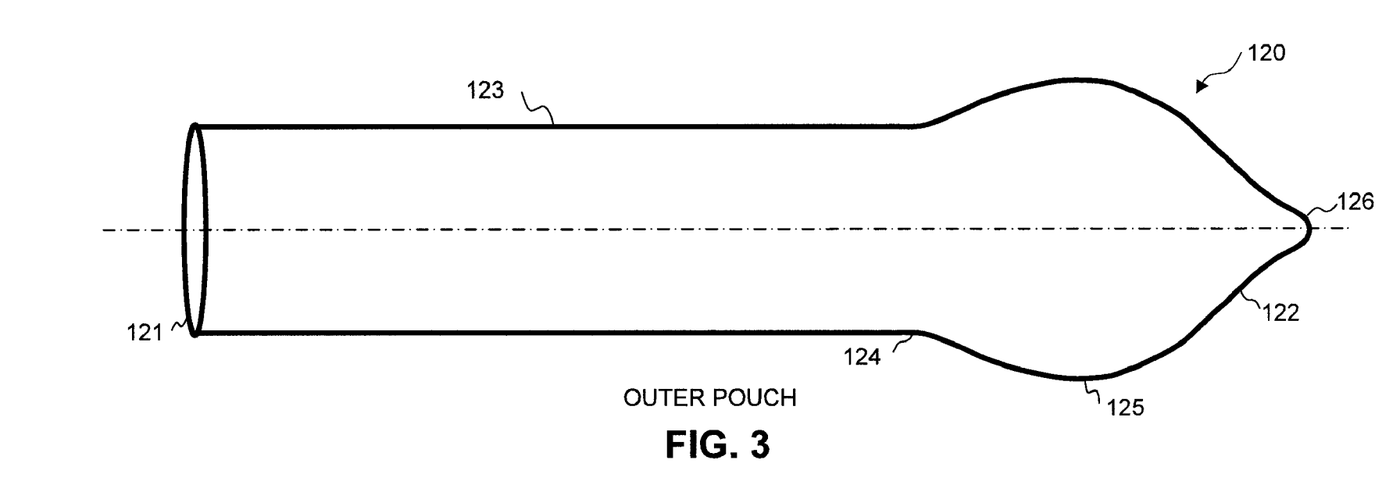
FIG. 3 illustrates an elevation view of the outer pouch of the condom of FIG. 1A.

FIGS. 1A-1E illustrate an exemplary embodiment of a condom 100 according to the invention. Condom 100 has a proximal open end 102 and a distal closed end 104, and includes an elongated hollow inner first pouch 110 disposed within an elongated hollow outer second pouch 120. Inner pouch 110 and outer pouch 120 are also illustrated in FIGS. 2 and 3, respectively. Inner pouch 110 includes a first open end 111 and a first closed end 112, with a first tubular body 113 extending distally from first open end 111 toward first closed end 112. Outer pouch 120 includes a second open end 121 and a second closed end 122, with a second tubular body 123 extending distally from second open end 121 toward second closed end 122.

First tubular body 113 of inner pouch 110 has a first large diameter segment 118 that extends distally to a first transition segment 119 that reduces in diameter to a narrow segment 109. First large diameter segment 118 has a diameter D1 at first open end 111 of pouch 110, which is generally the same as the diameter of outer pouch 120 at second open end 121. The diameter of first tubular body 113 is reduced distally of first open end 111 and may include a transition segment 119 where the diameter reduces to a diameter D2 at a proximal periphery 117 of narrow segment 109. Narrow segment 109 may be a constant diameter from proximal periphery 117 to a first neck portion 114 having a diameter D3. However, in other embodiments, diameter D3 may be slightly less than diameter D2. Distally of first neck portion 114, the diameter of inner pouch 110 increases to create a bulbous first head portion 115 having a diameter D4, which is approximately equal to or less than diameter D1 of first open end 111. First head portion 115 reaches a maximum diameter D4 and then decreases in diameter distally toward closed end 112, which may include a reservoir type tip 116.

Second tubular body 123 of outer pouch 120 may be generally cylindrical, having a diameter D5 along the length of second tubular body 123 that is approximately the same as diameter D1 of open end 111 of inner pouch 110, and that remains approximately constant from open end 121 until reaching a second neck portion 124, which is located generally adjacent to first neck portion 114 of inner pouch 110 when inner pouch 110 is disposed within outer pouch 120. Distally of second neck portion 124, the diameter of outer pouch 120 increases to create a bulbous second head portion 125 having a diameter D6 that is greater than diameter D4 of first head portion 115 of inner pouch 110. Second head portion 125 increases in diameter distally of second neck portion 124, reaches a maximum diameter D6, and then decreases in diameter distally to create closed end 122, which may include a reservoir type tip 126.

Typical condoms range between 160 to 180 mm or more in length. In the embodiment illustrated in FIGS. 1-3, outer pouch 120 is 180±10 mm in length and inner pouch 110 is about the same length as outer pouch 120 following assembly of inner pouch 110 with outer pouch 120. However, in some embodiments, inner pouch 110 may be molded to be 10-30 mm longer than outer pouch 120. Then, during assembly, the extra length of inner pouch 110 can be folded back over open end 121 of outer pouch 120 to form a reinforcement at sealed area 105. Additionally, in the embodiment illustrated, the first large diameter segment 118 is about one third the length of inner pouch 110, the narrow segment 109 is about one third the length of inner pouch 110, and first head portion 115 is about one third the length of inner pouch 110. Thus, in a preferred embodiment, narrow segment is 40±20 mm in length. This distributes the pressure created by the narrow segment and prevents uncomfortable circumferential pressure from concentrating on a small area of the users' penis. However, these relative segment lengths may vary substantially in other embodiments of the condom 100. For example, first large diameter segment 118 may be between 10 and 100 mm in length, while narrow segment 109 may also be between 10 and 100 mm. The length of first head portion 115 is less flexible and preferably about 30-60 mm, since the length of head portion 115 aids in properly positioning narrow segment 109 below the glans of the penis, as is discussed further below.

Figures 1A, 1B, 1C, 1D, 1E:
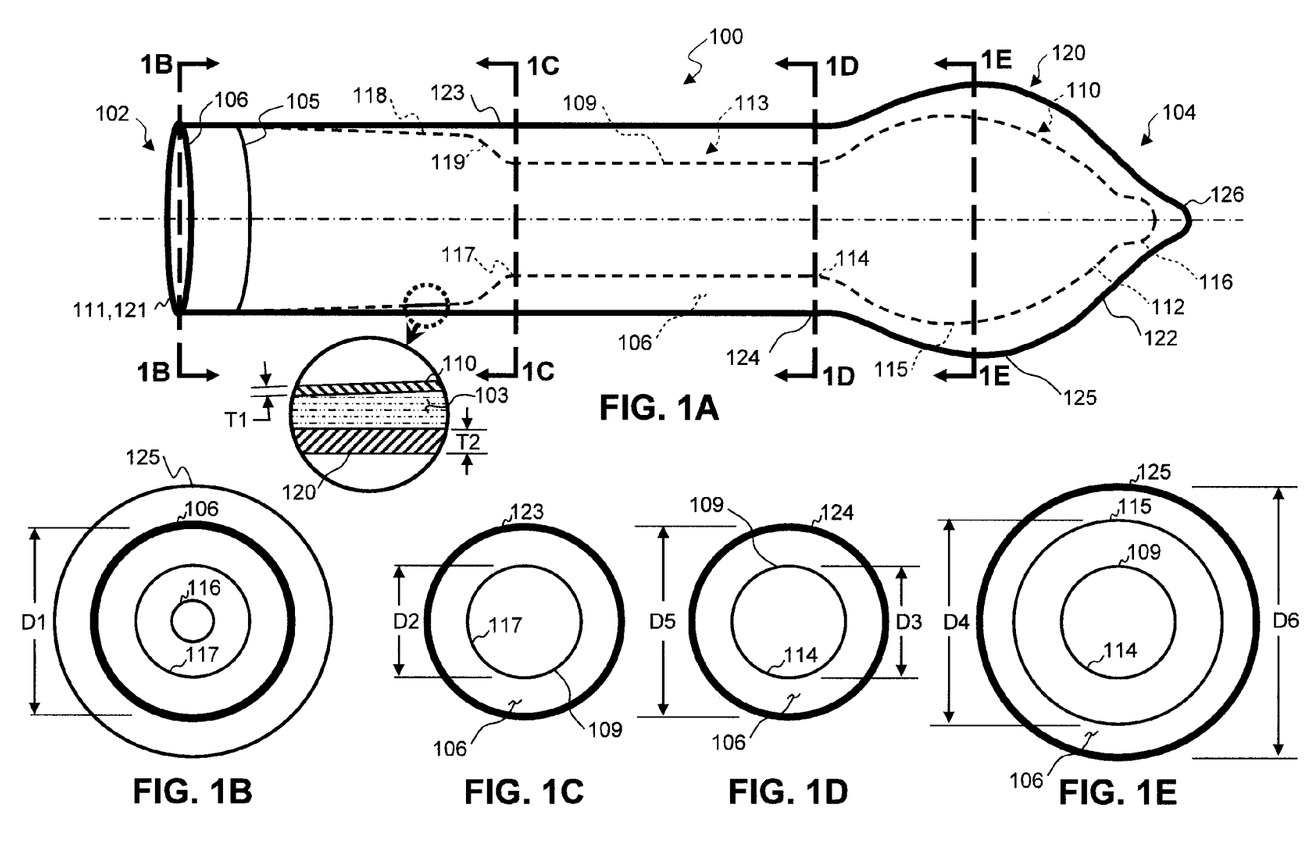
FIG. 1A illustrates an elevation view of an exemplary embodiment of a double-walled condom according to the invention.
FIG. 1B illustrates an end view of the open end of the condom of FIG. 1A as viewed from line 1B-1B.
FIG. 1C illustrates a cross section view taken along line 1C-1C of FIG. 1A.
FIG. 1D illustrates a cross section view taken along line 1D-1D of FIG. 1A.
FIG. 1E illustrates a cross section view taken along line 1E-1E of FIG. 1A.

As illustrated in FIGS. 1A and 1E, the diameter D6 of second head portion 125 is substantially larger than the diameter D4 of first head portion 115. For example, first head portion 115 may be of a diameter D4 to fit rather snuggly on the average erect human penis, while second head portion 125 may be of a diameter to be quite loose on the average erect penis, so that second head portion 125 of outer pouch 120 can freely slide back and forth relative to first head portion 115 of inner pouch 110 and the glans of the penis. In preferred embodiments, diameters D2 and D3 may be 26±4 mm; diameter D1 of first open end 111, diameter D4 of first head portion 115 of inner pouch 110, and diameter D5 of outer tubular body 123 may be 32±4 mm; and the diameter D6 of outer pouch 120 may be 42±6 mm. Thus, in some embodiments, the diameters D1, D4 and D5 are about 75 percent of the diameter D6. Also, in other embodiments, the relative diameters of D1, D2, D3, D4, D5 and D6 may vary from those set forth above. Additional significance and utility of the relative diameters D1-D6 of the portions of inner pouch 110 and outer pouch 120 is discussed further below.

Inner pouch 110 and outer pouch 120 are each constructed from an elastic, flexible and resilient film material, such as latex, polyurethane, or the like. Techniques for manufacturing inner pouch 110 and outer pouch 120 include dip molding, whereby forms having the desired configuration for each of the inner pouch 110 and the outer pouch 120 are dipped into a tank of the elastic material in liquid state, so that uniform films are produced over the forms. The films set and are then removed from the forms to serve as the inner pouch and outer pouch. Inner pouch 110 and outer pouch 120 are sealed to each other at a sealed area 105 located at, and optionally extending distally adjacent to, open end 102 of condom 100, using an adhesive, heat seal, ultrasonic weld, or the like. Sealed area 105 may be confined to a ring-shaped bead 106 located at open end 102, or sealed area 105 may extend distally from open end 102 along the length of tubular bodies 113, 123, as illustrated in FIG. 1A, thereby encompassing part of tubular bodies 113, 123. For example, in some embodiments, sealed area 105 may extend from 10-100 mm distally from open end 102.

Condom 100 and pouches 110, 120 are illustrated in FIGS. 1-3 in an as-molded configuration for purposes of illustration and discussion of various relative dimensions. However, during assembly of condom 100, when inner pouch 110 is placed within outer pouch 120, and prior to completing sealing of sealed area 105, negative pressure is created between inner pouch 110 and outer pouch 120 to remove any air pockets. Further, a lubricant 103, optionally including a silicon lubricant, spermicidal, antiseptic, antibacterial, and/or antiviral agent, is disposed in the interstitial area 106 between the inner pouch 110 and outer pouch 120 to enable smooth gliding of outer pouch 120 over inner pouch 110. For example, one cc of liquid lubricant may be used in the interstitial area 106 for each condom 100, and an additional quantity of lubricant may be added to the exterior of condom 100 to improve ease of donning the condom and insertion into a vagina. The negative pressure created between the two pouches 110, 120 causes outer pouch 120 to bunch or cling around inner pouch 110 in a collapsed configuration thereby maximizing contact of the outer pouch with the inner pouch, and enables the pouches to generally function as a single unit except toward the distal end 104, where, because of the larger relative diameters of the neck and head portions 124, 125 of outer pouch 120, the outer pouch has a slack portion that enables the outer pouch to easily slide back and forth over the inner pouch to create pleasurable sensations. This pleasurable effect is enhanced because the narrow segment 109 causes the inner the pouch to be locked over the penis during intercourse, or, in other words, the constriction of the narrow segment prevents the inner pouch from sliding relative to the shaft of the user's penis during intercourse, while the outer pouch is able to slide relative to both the penis and the inner pouch.

Conventional condoms typically have a wall thickness of 0.06-0.08 mm, while the so called "ultra sensitive" condoms have wall thicknesses between 0.04 and 0.05 mm. In embodiments of the present invention, inner pouch 110 is preferably constructed having a wall thickness T1 that is thinner than a wall thickness T2 of outer pouch 120. In some embodiments, inner pouch 110 has a wall thickness T1 of 0.06 mm or less and outer pouch 120 has a wall thickness T2 of 0.08 mm or more. Under such a configuration, the inner pouch is thin, thereby providing maximum sensitivity to the user, while the outer pouch is as thick, or thicker, than a conventional condom, thereby providing additional protection against breakage, since the outer pouch is able to withstand a large amount of stress. The sliding action of the outer pouch 120 against the inner pouch 110 increases pleasure to the user because inner pouch 110 is thin, providing high sensitivity, while the presence of the lubricant 103 and the relatively larger diameters of the neck and head portions 124, 125 of the outer pouch enable outer pouch 120 to slide back and forth over the inner pouch 110 which is maintained relatively immobile on the penis during intercourse due to the gripping action of narrow segment 109. In other higher strength embodiments, inner pouch 110 has a wall thickness T1 that is less than 0.10 mm and outer pouch 120 has a wall thickness that is thicker than inner pouch 110 and that is less than 0.20 mm. Further, because each of inner pouch 110 and outer pouch 120 serve as redundant protection against breakage or pinholes in the other pouch 110, 120, should one of the inner or outer pouches fail, the other of the pouches still functions to prevent pregnancy and transmission of STDs.

Additionally, studies in the US have shown that the circumference of the erect penis of the majority of adult human males is between 3.9 and 5 inches (99-127 mm), which equals an average diameter between 1.24 and 1.59 inches (31-40 mm). The inner pouch 110 of the invention includes narrow segment 113 which terminates in first neck portion 114 that is intended to be positioned just behind (i.e., below and adjacent to) the glans of the user's penis when the condom 100 is put on. In embodiments of the invention, the diameter D2 of narrow segment 113 and first neck portion 114 is substantially less than the diameter of the average erect adult penis so as to apply a pressure to the area below the glans of the penis and adjacent to the penile frenulum. In some preferred embodiments, the diameter D2 of the first neck portion 114 of inner pouch 110 is 26±4 mm, and preferably about 24 mm. The inventor has found that the narrow segment 113 of inner pouch 110 of condom 100 of the invention applies a circumferential squeezing pressure on the penis just below the glans of the penis, in the vicinity of the penile frenulum, which is able to produce results similar to the so called "squeeze technique" for preventing premature ejaculation developed by the American sex therapists Masters and Johnson. (See, e.g., Masters W H, Johnson V E., Human Sexual Inadequacy, Boston: Little, Brown & Co., 1970, which is incorporated herein by reference.) Thus, the condom 100 of the invention is able to increase the length of time of sexual intercourse by inhibiting premature ejaculation due to the narrow segment overlying and applying pressure to the penile frenulum, while the sliding action of the outer pouch 120 over the thinner inner pouch 110 creates a uniquely pleasurable sensation for both users.

Further, first head portion 115 of inner pouch 110 has a diameter D4 that may be sized larger or smaller to increase or decrease the amount of pleasure experienced by the wearer of the condom, while the diameter of narrow segment 109 can also be adjusted to control the degree of squeezing effected. For example, first head portion 115 may have a diameter D4 of 28 mm that will fit tightly on the average human penis, while narrow segment 109 may have a diameter D3 of 24 mm or less. This configuration will create an inner pouch that fits tightly on the average human penis and that applies a circumferential squeezing pressure in the area of the penile frenulum and glans that has an inhibiting effect on premature ejaculation, but also results in slightly reduced pleasure for the user. On the other hand, as another example, when first head portion has a diameter D4 of 36 mm and narrow segment 109 has a diameter D3 of 24-28 mm, the pleasure experienced by the user is greater because first head portion 115 is able to slide relative to the glans of the penis, while the remainder of the inner pouch 110 is held immobile due to the circumferential pressure applied by narrow segment 109. Further, the circumferential pressure applied by narrow segment 109 in the area below the glans penis at the location of the penile frenulum is still able to have an inhibiting effect on premature ejaculation. Accordingly, it may be seen that the dimensions of the inner pouch may be tailored to achieve varying effects in increasing or decreasing pleasure and in inhibiting premature ejaculation.

Additionally, in alternative embodiments, the inner pouch 110 may be used independently of the outer pouch 120 as a standalone condom, but in such cases, a number of advantages of condom 100 will be lost, including the additional protection against breakage provided by the outer pouch, and the added sensation due to the sliding action of the outer pouch 120 over the inner pouch and glans of the penis. Furthermore, the sizes and dimensions given above are intended to accommodate the range of the average human penis, as discussed above. It will be apparent that the relative dimensions of the condom 100 of the invention may be adjusted to create a larger or smaller overall condom able to produce the same beneficial attributes to enable the condom to fit properly, as described, on men having larger or smaller penises than average, respectively.

Guide

FIGS. 4A-4B and 5A-5B illustrate a condom guide 200 that serves as an aid in preventing condom 100 or any other condom from being applied inside out. Because the condom 100 of the invention includes an inner pouch 110 and an outer pouch 120 that are distinct in structure, purpose and function, it is important that condom 100 not be applied inside out. However, condom 100 is rolled like a conventional condom for use, and so there is a risk that condom 100 might be put on incorrectly by a user. In order to reduce this risk a guide 200 may be provided and packaged with condom 100 to aid in proper application of condom 100.

Figure 4A:
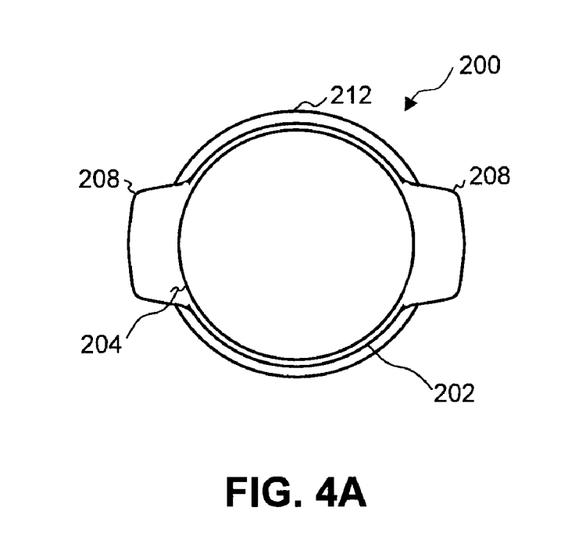
FIG. 4A illustrates a plan view of an exemplary embodiment of a guide that may be used with the condom of the invention.
Figure 4B:
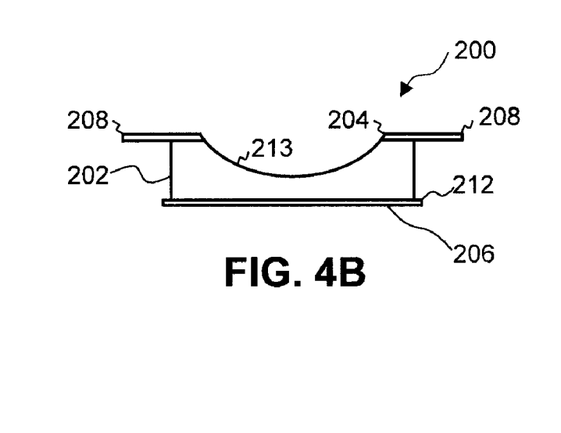
FIG. 4B illustrates an elevation view of the guide of FIG. 4A.

In a preferred embodiment, guide 200 includes a cylindrical body 202 having an upper first end 204 and a lower second end 206. A pair of opposed restrictors 208 extend outwardly in a wing-like manner perpendicularly from cylindrical body 202 at first end 204 and serve to prevent a rolled condom 210 from being unrolled from guide 200 in the incorrect direction.

Figures 5A, 5B:
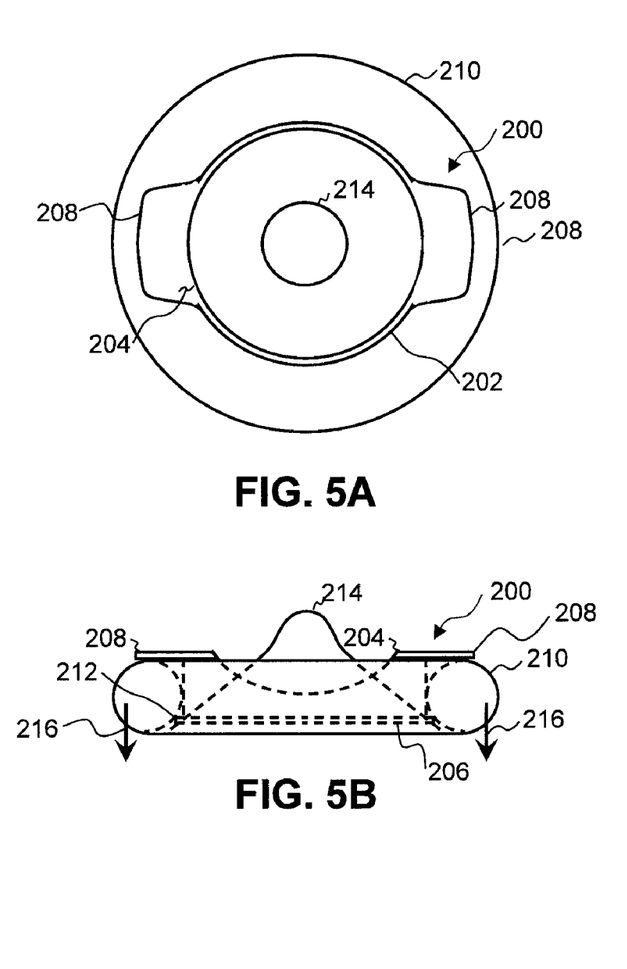
FIG. 5A illustrates a plan view of the guide of FIG. 4A with a condom installed thereon.
FIG. 5B illustrates an elevation view of the guide of FIG. 4B with a condom installed thereon.

An annular lip 212 is included at lower second end 206 to help retain rolled condom 210 on guide 200 until a user is ready to put on condom 210. The guide 200 is sized so that condom 210, in the rolled configuration, as illustrated in FIGS. 5A and 5B, will fit snuggly around cylindrical body 202, and be retained on cylindrical body 202 by annular lip 212. A pair of opposed arc-shaped cut outs 213 may be included in cylindrical body 202 to make it easier for a user to grasp and pinch the tip 214 of condom 210 while unrolling condom 210 onto a penis. Guide 200 may be constructed from plastic, such as from molded thermoplastic polymer, or other suitable material.

In use, condom 210 is preferably prepackaged and pre-mounted on guide 200. The user places guide 200 with rolled condom 210 mounted thereon on the end of the penis so that lower second end 206 of guide 200 is closest to the penis. The user then unrolls the condom onto the penis in the direction of arrows 216, while simultaneously pinching the tip 214 of condom 210 to remove any air from the tip. Once the condom has been unrolled off the guide 200, guide 200 may be discarded. If a user should attempt to unroll condom 210 onto the penis in the incorrect direction (i.e., opposite to arrows 216), it may be seen that restrictors 208 will prevent the condom from being unrolled in this direction. Further, should the user force the condom over restrictors 208, the guide will be trapped between the condom and the user's penis which will alert the user that that condom 210 is being applied incorrectly. Additionally, as mentioned above, while guide 200 is particularly useful for use with condom 100 of the invention, guide 200 may be used with any rolled condom for ensuring proper application, and is not limited to use with condom 100 described above.

Condom Having an Undulated Body

Figure 6A:
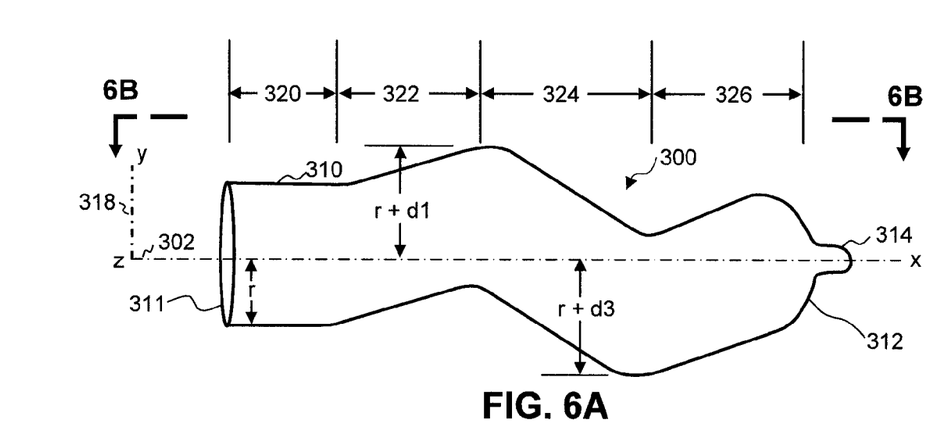
FIG. 6A illustrates another exemplary embodiment of a condom of the invention.
Figure 6B:
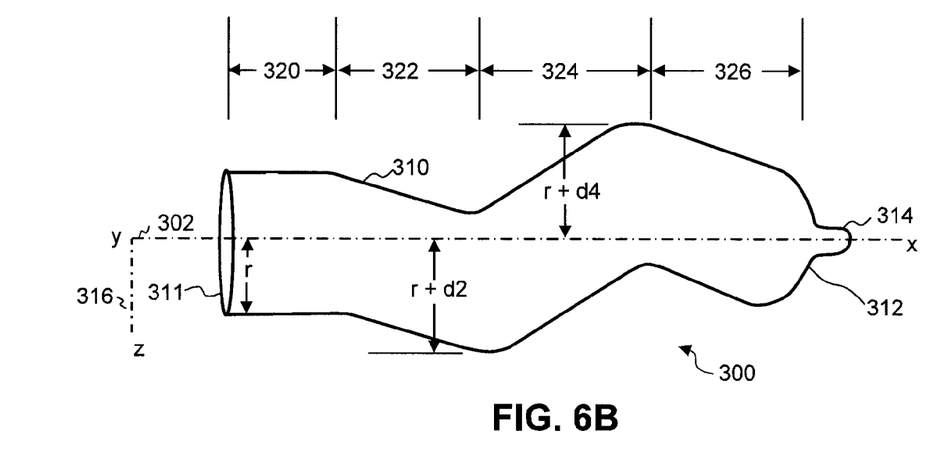
FIG. 6B illustrates a top view of the condom of FIG. 6A, as taken along line 6B-6B.

FIGS. 6A-6B illustrate another embodiment of a condom 300 having an undulated body configuration. Condom 300 consists of a hollow tubular body 310 having a proximal open end 311 and a distal closed end 312, with a distal tip 314. Tubular body 310 is undulated or in deviation from the center line 302, such that if centerline 302 forms an x axis in an xyz frame of reference, then in FIG. 6A, the z axis 316 is coming out of the page, and in FIG. 6B, the y axis 318 is coming out of the page. Thus, it may be seen that tubular body 310 undulates in multiple directions along its length. In the example illustrated, a first segment 320 is substantially parallel with centerline 302. A second segment 322 turns upward in the y direction a distance of d1, such that the distance d1 may be measured to the centerline 302 as the radius r of tubular body 310 at open end 311 plus distance d1. Additionally, second segment 322 also extends outward in the z direction a distance of r+d2 from the centerline 302. In the embodiment shown d1=d2, but this is not necessarily the case in other embodiments. A third segment 324 extends back in the minus y direction a distance of r+d3, while extending back in the minus z direction a distance of r+d4 from the centerline 302. In the embodiment shown d3=d4, but this is not necessarily the case in other embodiments. A fourth segment extends in the positive y and positive z directions again to return tip 208 to centerline 302. Condom 300 may be lubricated and rolled like a regular condom for easy application. The unique shape of condom 300 provides a pleasurable sensation to the user by creating areas of slack along the length of the condom, while other areas are stretched more tightly to maintain the condom in position.

Bellows Head Condoms

Figure 7:
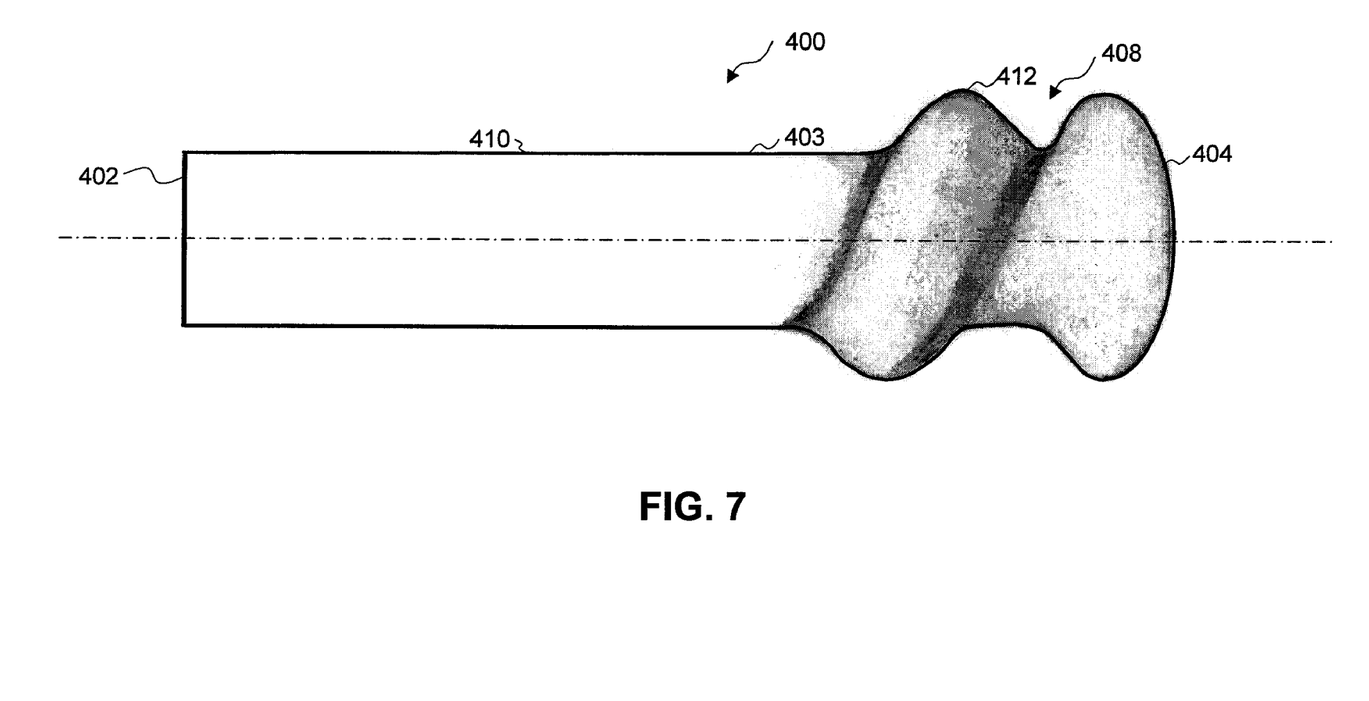
FIG. 7 illustrates another exemplary embodiment of a condom of the invention.
Figure 8:
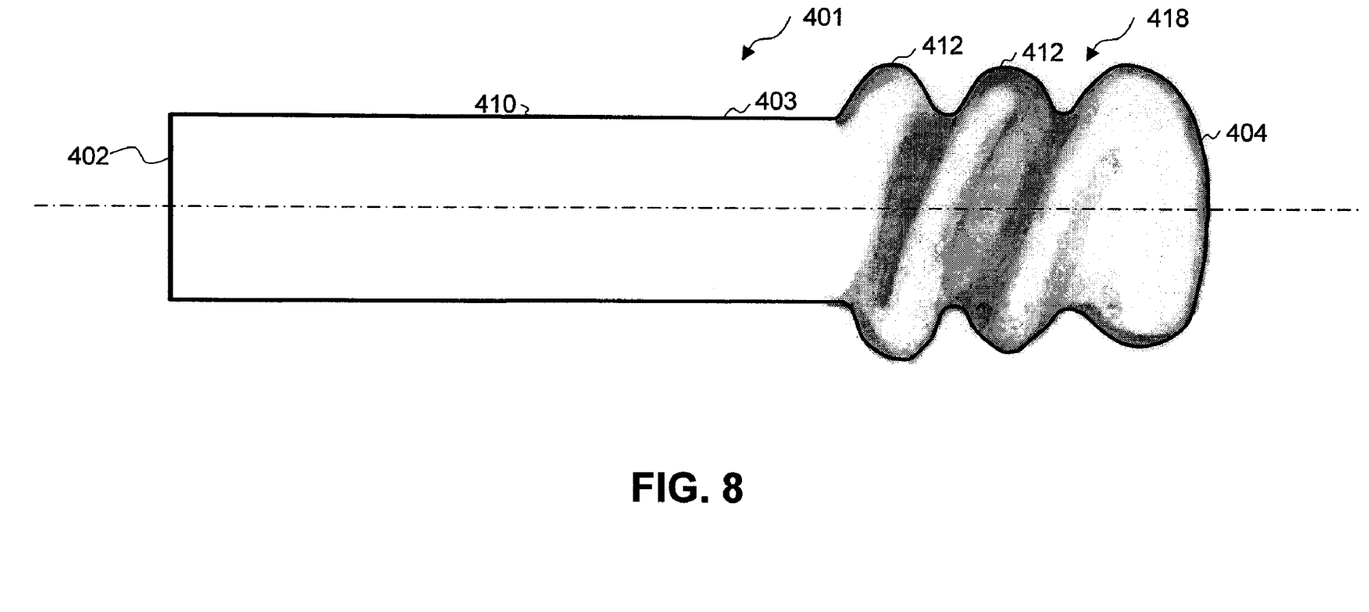
FIG. 8 illustrates another exemplary embodiment of a condom of the invention.

FIGS. 7 and 8 illustrate two exemplary embodiments of condoms having a bellows formed toward the closed end. As illustrated in FIG. 7, a condom 400 includes a pouch 403 having a proximal open end 402 and a distal closed end 404. Closed end 404 is a round flat slightly domed end, rather than having a conventional reservoir tip. Pouch 403 includes a tubular body portion 410 and an expanded bellows configuration 408 formed distally toward the closed end 404 of tubular body 410. Bellows configuration 408 is formed by a spiral shaped channel or bulge 412 that extends radially outward from tubular body 410 and that extends along the remaining length of pouch 403 in a spiral configuration. Spiral shaped bulge 412 is formed on condom 400, so that when condom 400 is placed on a user's penis, the bellows configuration 408 is positioned so as to begin below the glans of the penis. Bulge 412 is sufficiently larger in diameter than tubular body 410 that so that the bellows configuration 408 fits loosely on the end of the user's penis and is able to move freely back and forth, while tubular body 410 fits sufficiently snuggly around the shaft of the user's penis to prevent slippage of the condom from the base of the penis. For example, in some embodiments, tubular body 410 may be 34 mm in diameter, while bulge 412 forming bellows 408 the closed end 404 may be 51-55 mm in diameter. During use, the bellows configuration 408 moves back and forth (i.e., expands and contracts) with each thrust made during intercourse, thereby providing additional pleasurable stimulation to both partners.

FIG. 8 illustrates a condom 401, similar to condom 400 described above, and having a bellows configuration 418 formed toward the distal end 404 thereof. Condom 401 includes two spiral shaped bulges 412, and functions in a manner similar to condom 400 described above. Bellows configuration 418 may be of a diameter similar to bellows configuration 408 of condom 400, and thus, in some embodiments, tubular body 410 may be 34 mm in diameter, while bulges 412 forming bellows 418 and closed end 404 may be from 51-55 mm in diameter. Further either of condoms 400, 401 may be used as the outer pouch 120 in the embodiment of FIGS. 1A-1E, thereby providing even greater sliding sensation caused by outer pouch 120.

Thus, it may be seen that the inventive condoms described above provide improved and extended pleasure to the users, and also can decrease the likelihood of failure. Further, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the above description has been made in an illustrative fashion, and not a restrictive one. Accordingly, the scope of the invention should properly be determined with reference to the appended claims, along with the full range of equivalents to which such claims are entitled.

What is claimed is:

1. A condom comprising:
a first pouch having a first open end and a first closed end, said first pouch being disposed within a second pouch, said second pouch having a second open end and a second closed end;
said first pouch being bonded to said second pouch adjacent to said first and second open ends to form a sealed interstitial space between the first and second pouches;
a lubricant being located in said interstitial space to enable said second pouch to slide relative to said first pouch;
said first pouch having a first wall thickness that is less than a second wall thickness of the second pouch; and
said first pouch having a narrow segment that is less than an average diameter of an erect human penis, said narrow segment applying circumferential pressure to an area below the glans of the penis when the condom is disposed on the penis of a user for inhibiting premature ejaculation for the user of the condom.

2. The condom according to claim 1,
wherein said first wall thickness is 0.10 mm or less and said second wall thickness is 0.20 mm or less and thicker than said first wall thickness.

3. The condom according to claim 1,
wherein said first wall thickness is 0.06 mm or less and said second wall thickness is 0.08 mm or more.

4. The condom according to claim 1, further comprising:
said first pouch having a first tubular body, said first tubular body having a first diameter segment having a first diameter at said first open end, said first tubular body transitioning distally of said first opening to a second diameter at a proximal periphery of a narrow segment, said narrow segment extending distally to a first neck portion of said first pouch, said first neck portion having a third diameter, said narrow segment being between 10 and 100 mm in length, said first tubular body transitioning to a fourth diameter distally of said first neck portion at a first head portion of said first pouch and then transitioning to said first closed end.

5. The condom according to claim 4,
wherein said second diameter and said third diameter are less than said first diameter and said fourth diameter, the portion of said first tubular body extending between said second diameter and said third diameter comprising said narrow segment, and being less than an average diameter of an erect human penis,
wherein, when said condom is disposed on the penis, said first neck portion is located immediately below the glans of the penis and said narrow segment applies said circumferential pressure.

6. The condom according to claim 5,
wherein said second pouch has a second tubular body, said second tubular body having a second neck portion located in the vicinity of said first neck portion when said first pouch is disposed within said second pouch, said second neck portion having a fifth diameter that is greater than said third diameter of said first neck portion, said second neck portion transitioning to a sixth diameter distally of said second neck portion at a second head portion and then transitioning to said second closed end,
wherein said fourth diameter at said first head portion is 76 percent or less than the sixth diameter at said second head portion so that said second pouch is able to easily slide back and forth relative to said first pouch at said second head portion due to back and forth movement of the penis and the condom during intercourse.

7. The condom according to claim 6,
wherein said sixth diameter is 42 mm or more and said fourth diameter is 32 mm or less.

8. The condom according to claim 1,
wherein said first pouch is bonded to said second pouch at a bonded area adjacent to said first and second open ends, said bonded area extending distally of said first and second open ends between 10 and 100 mm.

9. The condom according to claim 1,
wherein the interstitial space between said first pouch and said second pouch is under negative pressure so that said second pouch clings around said first pouch in a collapsed configuration.

10. A condom comprising:
a first pouch having a first open end and a first closed end, said first pouch being disposed within a second pouch, said second pouch having a second open end and a second closed end, said first pouch being bonded to said second pouch adjacent to said first and second open ends to form a sealed interstitial space between the first and second pouches;
a lubricant located in said interstitial space to enable said second pouch to slide relative to said first pouch;
said first pouch having a first tubular body, said first tubular body having a first diameter segment having a first diameter at said first open end, said first tubular body transitioning distally of said first opening to a second diameter at a proximal periphery of a narrow segment, said narrow segment extending distally to a first neck portion of said first pouch, said first neck portion having a third diameter, said narrow segment being between 10 and 100 mm in length, said first tubular body transitioning to a fourth diameter distally of said first neck portion at a first head portion of said first pouch and then transitioning to said first closed end,
wherein said second diameter and said third diameter are less than said first diameter and said fourth diameter, the portion of said first tubular body extending between said second diameter and said third diameter comprising said narrow segment, and being less than an average diameter of an erect human penis,
wherein, when said condom is disposed on the penis, said first neck portion is located below the glans of the penis and said narrow segment applies circumferential pressure to the vicinity of the penile frenulum for inhibiting premature ejaculation for a user of the condom said first pouch having a first wall thickness that is less than a second wall thickness of the second pouch.

11. The condom according to claim 10,
wherein said first pouch has a wall thickness of 0.06 mm or less and said second pouch has a wall thickness of 0.08 mm or more.

12. The condom according to claim 10,
wherein said first wall thickness is 0.10 mm or less and said second wall thickness is 0.20 mm or less and thicker than said first wall thickness.

13. The condom according to claim 10,
wherein said first diameter is 32±4 mm, and
wherein said second diameter and said third diameter are 8±4 mm less than said first diameter.

14. The condom according to claim 10, further comprising:
said second pouch having a second tubular body, said second tubular body having a second neck portion located in the vicinity of said first neck portion when said first pouch is disposed within said second pouch, said second neck portion having a fifth diameter that is greater than said third diameter of said first neck portion, said second neck portion transitioning to a sixth diameter distally of said second neck portion at a second head portion and then transitioning to said second closed end,
wherein said fourth diameter at said first head portion is 76 percent or less than the sixth diameter at said second head portion so that said second pouch is able to easily slide back and forth relative to said first pouch at said second head portion during intercourse.

15. The condom according to claim 10,
wherein said first pouch is bonded to said second pouch at a bonded area adjacent to said first and second open ends, said bonded area extending distally of said first and second open ends between 10 and 100 mm, and
wherein the interstitial space between said first pouch and said second pouch is under negative pressure so that said second pouch clings around said first pouch in a collapsed configuration.

16. A condom comprising:
a first pouch having a first open end and a first closed end, said first pouch being disposed within a second pouch, said second pouch having a second open end and a second closed end,
said first pouch being bonded to said second pouch adjacent to said first and second open ends to form a sealed interstitial space between the first and second pouches;
a lubricant located in said interstitial space to enable said second pouch to slide relative to said first pouch;
said first pouch having a first wall thickness that is less than a second wall thickness of the second pouch;
said first pouch having a first tubular body, said first tubular body having a first diameter segment having a first diameter at said first open end, said first tubular body transitioning distally of said first opening to a second diameter at a proximal periphery of a narrow segment, said narrow segment extending distally to a first neck portion of said first pouch, said first neck portion having a third diameter, said narrow segment being between 10 and 100 mm in length, said first tubular body transitioning to a fourth diameter distally of said first neck portion at a first head portion of said first pouch and then transitioning to said first closed end,
wherein said second diameter and said third diameter are less than said first diameter and said fourth diameter, said third diameter being less than an average diameter of an erect human penis,
wherein, when said condom is disposed on the penis, said first neck portion is located below the glans of the penis, and said narrow segment applies circumferential pressure to the vicinity of the penile frenulum for inhibiting premature ejaculation for a user of the condom; and
said second pouch having a second tubular body said second tubular body having a second neck portion located in the vicinity of said first neck portion when said first pouch is disposed within said second pouch, said second neck portion having a fifth diameter that is greater than said third diameter of said first neck portion, said second neck portion transitioning to a sixth diameter distally of said second neck portion at a second head portion and then transitioning to said second closed end,
wherein said fourth diameter at said first head portion is 76 percent or less than the sixth diameter at said second head portion so that said second pouch is able to easily slide back and forth relative to said first pouch at said second head portion during intercourse, thereby providing stimulation to the glans of the penis.

17. The condom according to claim 16,
wherein said sixth diameter is 42 mm or more and said fourth diameter is 32 mm or less.

18. The condom according to claim 16,
wherein said first pouch is bonded to said second pouch at a bonded area adjacent to said first and second open ends, said bonded area extending distally of said first and second open ends between 10 and 100 mm, and
wherein the interstitial space between said first pouch and said second pouch is under negative pressure so that said second pouch clings around said first pouch in a collapsed configuration.

19. The condom according to claim 16,
wherein said first wall thickness is 0.10 mm or less and said second wall thickness is 0.20 mm or less and thicker than said first wall thickness.

* * * * *